(12) United States Patent
Kunitake et al.

(10) Patent No.: US 8,608,664 B2
(45) Date of Patent: Dec. 17, 2013

(54) ELECTRODE

(75) Inventors: Takato Kunitake, Miyazaki (JP); Hiroshi Kannan, Miyazaki (JP)

(73) Assignee: University of Miyazaki, Miyazaki (JP)

( * ) Notice: Subject to any disclaimer, the term of this patent is extended or adjusted under 35 U.S.C. 154(b) by 90 days.

(21) Appl. No.: 13/000,221

(22) PCT Filed: Jun. 19, 2009

(86) PCT No.: PCT/JP2009/061665
§ 371 (c)(1),
(2), (4) Date: Feb. 28, 2011

(87) PCT Pub. No.: WO2009/154308
PCT Pub. Date: Dec. 23, 2009

(65) Prior Publication Data
US 2011/0190656 A1 Aug. 4, 2011

(30) Foreign Application Priority Data
Jun. 20, 2008 (JP) .................................. 2008-161995

(51) Int. Cl.
*A61B 5/05* (2006.01)
(52) U.S. Cl.
USPC .......................................... 600/554; 607/446
(58) Field of Classification Search
USPC ............................................ 600/554; 607/46
See application file for complete search history.

(56) References Cited

U.S. PATENT DOCUMENTS

| | | | |
|---|---|---|---|
| 2004/0215237 A1* | 10/2004 | Christopherson et al. | 607/3 |
| 2005/0182457 A1* | 8/2005 | Thrope et al. | 607/48 |
| 2007/0103496 A1* | 5/2007 | Otani | 347/11 |
| 2008/0103496 A1 | 5/2008 | Christopherson et al. | |
| 2009/0069654 A1* | 3/2009 | Yasuzawa et al. | 600/345 |

FOREIGN PATENT DOCUMENTS

| | | |
|---|---|---|
| JP | 2006212133 A | 8/2006 |
| WO | 2006/059430 A1 | 6/2006 |
| WO | WO2007/091633 * | 6/2007 |
| WO | 2007/091633 A1 | 8/2007 |

OTHER PUBLICATIONS

Umeda, Minoru, et al.; "Porous-microelectrode study on Pt/C catalysts for methanol electrooxidation"; Electrochimica Acta; vol. 48, 2003; pp. 1367-1374.
Office Action corresponding to Chinese Patent Application No. 200980132458.X issued Dec. 5, 2012.

* cited by examiner

*Primary Examiner* — Max Hindenburg
*Assistant Examiner* — Renee Danega
(74) *Attorney, Agent, or Firm* — Sughrue Mion, PLLC

(57) ABSTRACT

An object of the present invention is to provide a microelectrode capable of recording action potentials of nerve cells-neurons as large-amplitude waveforms and being appropriate for multi-channeling. The electrode 1 of the present invention comprises a conductive linear core material 2, an insulating coating layer 3a with which the outer circumference of the linear core material is coated, and an extending part 3b formed by extending the end part of the coating layer on one tip side of the linear core material beyond the tip in the longitudinal direction of the linear core material, in which a cavity that opens in the extending direction is formed within the extending part.

10 Claims, 12 Drawing Sheets
(3 of 12 Drawing Sheet(s) Filed in Color)

Fig. 4
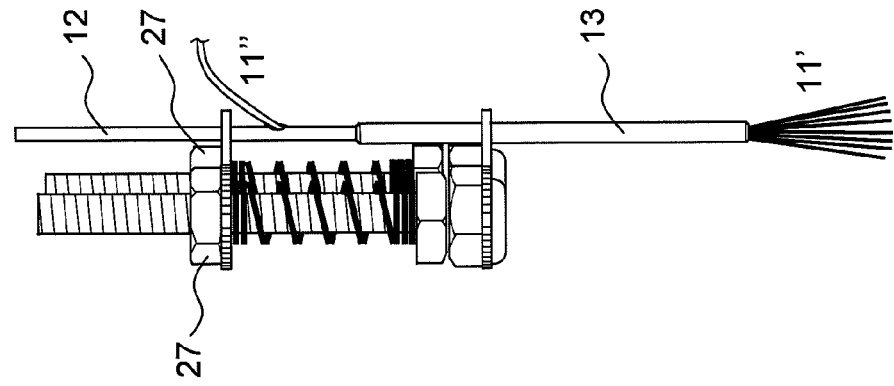
(a)
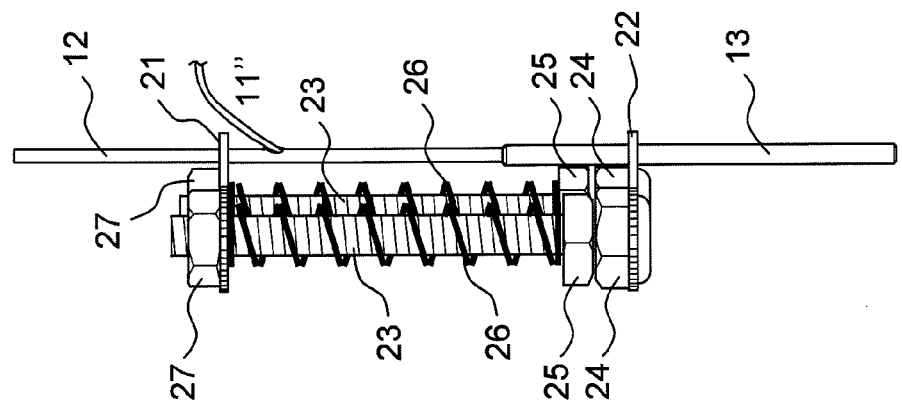
(b)

Fig. 7
(a)
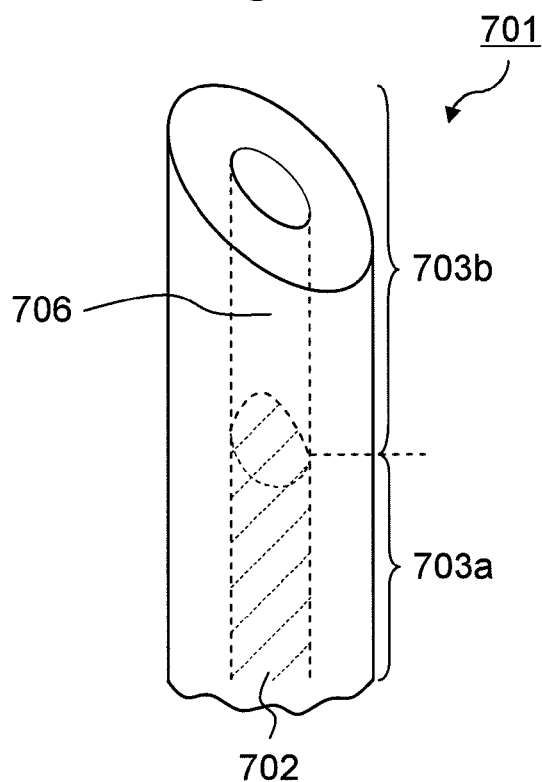
(b)
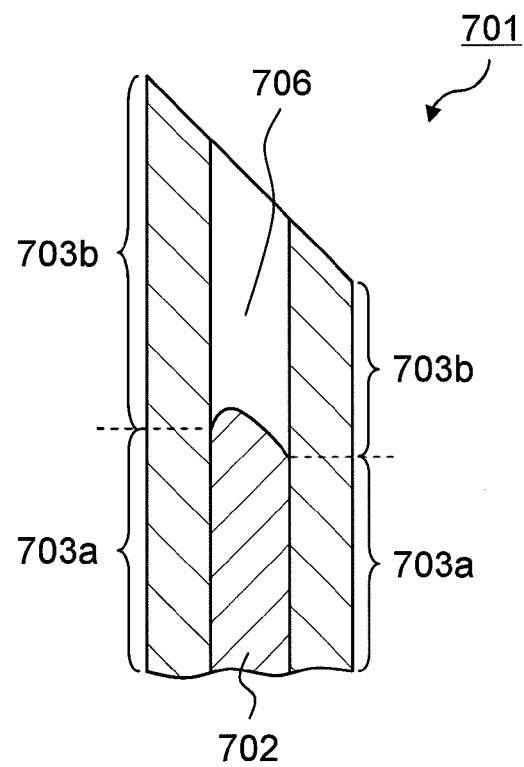

ELECTRODE

CROSS REFERENCE TO RELATED APPLICATIONS

This application is a National Stage of International Application No. PCT/JP2009/061665 filed Jun. 19, 2009, claiming priority based on Japanese Patent Application No. 2008-161995 filed Jul. 20, 2008, the contents of all of which are incorporated herein by reference in their entirety.

TECHNICAL FIELD

The present invention relates to an electrode that can be appropriately used for measuringnerve action or stimulating nerve cellsneurons in the brain or the like of an animal such as a human.

BACKGROUND ART

Measurement of the action of a single nerve of a freely moving animal is important for elucidation of brain functions. However, such measurement cannot be easily performed and efforts to do so have been ineffective.

A microelectrode that has been conventionally used for measuring nerve action potentialsaction potentialsneurons is produced by coating the outer circumference of a metal wire having a thickness ranging from about 20 μm to 80 μm with insulation paint and then cutting the metal wire with scissors or the like to expose the end parts. In general, a plurality of such microelectrodes are bundled and then used as a multi-channel electrode. When conventional microelectrodes are multi-channeled and then measurement is performed in neural population, the proportion of microelectrodes capable of recording nerve action is low (e.g., only 1 to 3 out of 8 microelectrodes can recordnerve action). Also, the waveform amplitude of action potentials recorded is small, which is about several times greater than the amplitude of the background noise (100-200 microvolts).

Patent document 1 and non-patent document 1 are presented as patent documents relating to the present invention.
Patent document 1 JP Patent Publication (Kokai) 2006-212133 A
Non-patent document 1 Umeda et. al, Electrochimica Acta, 48 (2003) 1367-1374

DISCLOSURE OF THE INVENTION

An object of the present invention is to provide a microelectrode capable of recording the action potentials of nerve cellsneurons in a large-amplitude waveform with respect to background noise.

Another object of the present invention is to provide a microelectrode with which a multi-channel electrode can be formed, such that when a plurality of microelectrodes are bundled for multi-channeling, differences in performance are insignificant among microelectrodes and nerve action potentialsaction potentialsneurons can be recorded by most of and preferably all microelectrodes. Conventionally, a microelectrode is generally produced by cutting a wire composed of a conductive core material and an insulating coating film that covers the conductive core material using scissors or the like so that it has a tip portion where the conductive core material is exposed. Microelectrodes that are produced by such a conventional method are problematic in that they have varied tip portion forms and different detection sensitivities. Accordingly, multi-channeling of conventional microelectrodes is problematic in that: only some of microelectrodes can record nerve action potentialsaction potentialsneurons (the number of microelectrodes capable of recording nerve action potentialsaction potentialsneurons is limited); and most of microelectrodes are unable to record action potentials. Therefore, it has been required to increase the number of electrodes to a greater extent than is necessary in view of the percent thereof that are defective. Another object of the present invention is to address such conventional technical problems.

The present inventors have surprisingly found that the above problems can be addressed with the following constitution.

(1) An electrode, comprising:
a conductive linear core material;
an insulating coating layer with which the outer circumference of the linear core material is coated; and
a part formed by extending the end part of the coating layer on one tip side of the linear core material beyond the tip in the longitudinal direction of the linear core material, and a cavity opening in the extending direction is formed within the part.
(2) The electrode according to (1), which is used for measuring nerve action or stimulating nerve cellsneurons.
(3) The electrode according to (1) or (2), wherein an end in the extending direction of the part is located on a single plane vertical to the shaft center of the linear core material and is formed so that the outer diameter of the end part in the extending direction of the extending part decreases along the extending direction.
(4) The electrode according to (1) or (2), wherein the end part in the extending direction of the extending part is sharply pointed.
(5) The electrode according to any one of (1) to (4), wherein the minimum length of the inner surface of the extending part along the extending direction is 0.1 to 10 times the thickness of the linear core material.
(6) The electrode according to any one of (1) to (5), wherein the thickness of the linear core material ranges from 5 μm to 80 μm.
(7) The electrode according to (2), wherein nerve cellsneurons located outside the cavity and the tip of the linear core material within the cavity can be communicated with each other via an electrolyte solution when the electrode is used for measuring nerve action or stimulating nerve cellsneurons.
(8) A multi-channel electrode, comprising a combination of a plurality of the electrodes according to any one of (1) to (7).
(9) Anerve action measuring device, comprising at least one electrode according to any one of (1) to (7) as an element for measuringnerve action.
(10) A neuron stimulator, comprising at least one electrode according to any one of (1) to (7) as an element for stimulating nerve cellsneurons.

Effects of the Invention

The microelectrode of the present invention is capable of recording the action potentials of nerve cellsneurons as large-amplitude waveforms.

However, multi-channeling of the microelectrodes of the present invention results in an increased proportion of microelectrodes capable of recording action potentials. Actually in Example 1, when the microelectrodes of the present invention were multi-channeled, action potentials of neurons could be recorded by all electrodes. As described above, measurement efficiency can be significantly enhanced through multi-channeling of the microelectrodes of the present invention and measurement of nerve action potentialsaction potentialsneurons.

This description includes part or all of the contents as disclosed in the description and/or drawings of Japanese Patent Application No. 2008-161995, which is a priority document of the present application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 shows perspective views of a device for fine-adjusting multi-channel electrodes comprising a plurality of microelectrodes (8 microelectrodes) and a positioning means for freeladjusting the protruding length of the microelectrodes, which was produced and used in Examples.

FIG. 7 shows a perspective view (a) of a portion near the tip of an electrode of the present invention and a cross-section (b) along the longitudinaldirection.

FIG. 12A shows the real part of impedance found as complex number for each frequency. FIG. 12B shows the imaginary part of the same. FIG. 12C shows the phase angle formed by the real part and the imaginary part on a complex plane for each frequency. FIG. 12D is a Nyquist diagram in which the real part and the imaginary part (both 200 kΩ or less) found for each frequency are both plotted.

EXPLANATION OF DATA SERIES IN THE FIGURE

Figure 1:
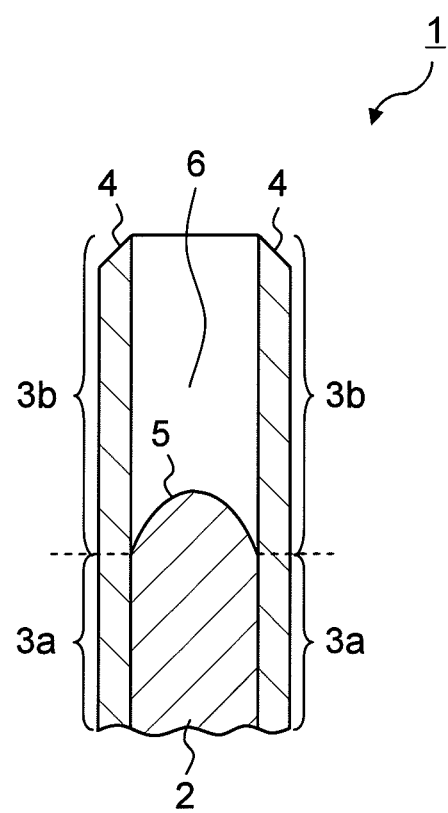
FIG. 1 shows a cross-section along the longitudinaldirection of a portion near the tip of an electrode of the present invention.

Cut: primary electrode; File: secondary electrode; 3 min: electrode (electrolysis time: 3 minutes) of the present invention; 15 min: electrode (electrolysis time: 15 minutes) of the present invention; 20 min: electrode (electrolysis time: 20 minutes) of the present invention; 30 min: electrode (electrolysis time: 30 minutes) of the present invention; and 50 min: electrode (electrolysis time: 50 minutes) of the present invention

EXPLANATION OF LETTERS AND NUMERALS 1 and 701 . . . Electrode
2 and 702 . . . Linear core material
3' . . . Initial coating layer
3a and 703a . . . Coating layer
3b and 703b . . . Extendingpart
4 . . . Tapered surface
5 . . . Tapered surface
6 and 706 . . . Cavity
101 . . . Primary electrode
102 . . . Secondary electrode
10 . . . Multi-channel electrode fine-adjusting device
11 . . . Microelectrode
11' . . . Protruding portion of microelectrode
11" . . . Rear end portion of microelectrode
12 . . . Internal sheath tube
13 . . . External sheath tube
14 . . . Tip opening of internal sheath tube
15 . . . Tip opening of external sheath tube
16 . . . Side wall opening of internal sheath tube
17 . . . Adhesive
21 . . . First support plate
22 . . . Second support plate
23 . . . Bolt
24 . . . Nut for fixing bolt head
25 . . . Nut for supporting spring
26 . . .
80 . . . Electrolyte solution
81 . . . Nerve tissue
900 . . . Nerve action measuring device
1000 . . . Neuron stimulator
1100 . . . Nerve action measuring/neuron stimulating device
901, 1001, and 1101 . . . Electrode
902 and 1102 . . . Amplifier
903 and 1103 . . . Preamplifier
904 and 1104 . . . Main amplifier
905, 1005, and 1105 . . . Arithmetic processing unit
906, 1006, and 1106 . . . Display device
907, 1007, and 1107 . . . Memory
908, 1008, and 1108 . . . Input device
950, 1050, and 1150 . . . Nerve tissue
1010 and 1110 . . . Electrical stimulation signal applying device

BEST MODE FOR CARRYING OUT THE INVENTION

The electrode of the present invention is as described below with reference to the following figures. FIG. 1 shows a cross-section along the longitudinaldirection near the tip of an electrode 1.

The electrode 1 of the present invention comprises a conductive linear core material 2, an insulating coating layer 3a with which the entire outer circumference of the linear core material 2 is coated, and an extending part 3b of the tip part. The extending part 3b is formed by extending the entire end part of the coating layer 3 on one tip side of the linear core material 2 toward the longitudinal direction of the linear core material so that the end part extends beyond the tip. Specifically, the extending part 3b has a tubular shape, in which a cavity 6 that opens in the extending direction is formed. In an embodiment of the present invention, the coating layer 3a and the extending part 3b are integrally formed, so that they are formed with the same materials and have the same inner diameter and the same outer diameter.

The inner diameter of the extending part 3b is identical identicalto the outer diameter of the linear core material 2. The outer diameter of the extending part 3b is preferably configured so that the outer diameter of the end part of the extending part 3b decreases in the extending direction, thereby forming a tapered surface 4.

In an embodiment of the present invention, the outer diameter of the tip part of the linear core material 2 is configured so that it decreases in the tip direction, thereby forming a tapered surface 5. In another embodiment (not shown) of the present invention, the outer diameter of the tip part of a linear core material is configured so that it does not decrease in diameter, resulting in a flat tip surface.

FIG. 1 relates to an embodiment wherein the end in the extending direction of an extending part is configured so that it is located on a single plane vertical to the shaft center of the linear core material, but embodiments are not limited thereto.

In another embodiment of the present invention, the end part in the extending direction of the extending part is sharply pointed. An example of the structure of the electrode tip part in this embodiment is described based on FIG. 7. FIG. 7(*a*) shows a perspective view near the tip of an electrode 701 and FIG. 7(*b*) shows a cross sectional view near such tip. An extending part 703b has a tubular shape and one end thereof is cut to result in an end surface slanted obliquely relative to the shaft center of a linear core material 702.

Explanation in this Description applies to both the embodiment in FIG. 1 and the embodiment in FIG. 7, unless specified.

The minimum length in the extending direction of the inner surface (that is, the surface of the cavity 6 or 706) of the extending part 3b or 703b is preferably 0.1 to 10 times and further preferably 0.5 to 8 times greater than the thickness of the linear core material 2 or 702. Different minimum lengths in the extending direction result in different volumes within the cavities of tip parts. Accordingly, the impedance resulting from an electrolyte solution with which each cavity is filled is varied depending on the above rate upon use. When the minimum length in the extending direction of the inner surface of the extending part is within the above specific range with respect to the thickness of the linear core material, the impedance change in the electrode of the present invention results in increased measurement sensitivity.

Materials that configure the linear core material 2 or 702 are not particularly limited, as long as they are conductive materials. Typical examples of such materials include nichrome, tungsten, stainless steel, and platinum-iridium. The thickness of the linear core material ranges from 5 μm to 80 μm, for example. The length of the linear core material 2 or 702 can be appropriately varied according to measurement sites, for example. The length is typically about dozens of centimeters or ranges from 10 cm to 20 cm, for example, as long as an electrode tip can reach a site where nerve action measurement or stimulation of nerve cellsneurons is performed. The term "linear" refers to a long and thin shape with a length sufficiently greater than the thickness (e.g., 10 times or more and typically 50 times or more). The linear core material may have any cross sectional shape. Typically, a linear core material having a circular (true circle or ellipse) cross-section or a linear core material having a polygonal cross-section (e.g., a tetragon) is used. The thickness of the linear core material is the maximum width of the transverse section vertical to the longitudinal axis of the linear core material. As the thickness of the linear core material, the thickness of a part of the linear core material can be employed. Specifically, the part of the linear material the thickness of which is employed herein is located closest to the tip side (where the extending part is formed in the longitudinal direction) in which the whole circumference of the cross-section of the part is coated with an insulating coating layer. For example, the above ratio of the minimum length of the inner surface (in the extending direction) of the extending part 3b or 703b to the thickness of the linear core material may be calculated based on the thickness of a portion of the linear core material 2 or 702 (in which the whole circumference of the cross-section is coated with the coating layer 3a or 703a) located closest to the tip side in the longitudinal direction.

Materials that configure the coating layer 3a or 703a and extending part 3b or 703b are not particularly limited, as long as they are insulating materials. Resins such as an epoxy resin are preferably used, since they can form films that have enough strength to avoid breakage or deformation when inserted into nerve tissue such as the brain. The coating layer 3a or 703a and the extending part 3b or 703b preferably have thickness ranging from 3 μm to 20 μm.

Any form of electrode may be encompassed within the scope of the present invention, as long as the tip part of the relevant electrode has the above characteristics of the microelectrode according to the present invention. For example, a conductive portion has the above linear portion at least on the tip side and may further contain, in addition to the linear portion on the tip side, a portion with an increased diameter for the purpose of enhancing mechanical strength.

Multi-channeling is possible through a combination of a plurality of the electrodes 1 or 701 of the present invention. Hereinafter, an electrode 1 or 701 of the present invention may be referred to as a "microelectrode," and an electrode formed of a combination of a plurality of the microelectrodes may be referred to as a "multi-channel electrode." Forms and methods for disposing microelectrodes when a plurality of microelectrodes are combined are not particularly limited and are selected according to purpose.

A plurality of microelectrodes may be disposed so that gaps are formed between the side faces of adjacent microelectrodes or so that the side faces of adjacent microelectrodes are closely attached to each other, for example. Also, the two forms of disposition may be combined. In an example of the embodiment in which microelectrodes are disposed so that gaps are formed between the side faces of adjacent microelectrodes, a plurality of microelectrodes are provided protruding like needles of a pinholder on a single plane, so that they are parallel to each other leaving gaps without allowing the side faces to come into contact with each other and tips are oriented in the same direction (e.g., see U.S. Pat. No. 5,215, 088). Examples of an embodiment wherein microelectrodes are disposed so that the side faces of adjacent microelectrodes are closely attached to each other include an embodiment wherein a plurality of microelectrodes are bundled in parallel and an embodiment wherein a plurality of microelectrodes are twisted together. In such embodiments, microelectrodes may be further closely attached to each other. An embodiment shown in FIG. 3(*a*) is an example of a combination of an embodiment wherein microelectrodes are disposed so as to form gaps between side faces of adjacent microelectrodes and an embodiment wherein microelectrodes are disposed so that the side faces of adjacent microelectrodes are closely attached to each other. In the embodiment in FIG. 3(*a*), at the tip portion, gaps are formed among side faces of microelectrodes, but at the other portions, microelectrodes are closely attached to each other.

Disposition of the tips of a plurality of multi-channel microelectrodes can be determined according to purpose. For example, at least one of the tips of a plurality of microelectrodes may be disposed at a position differing from those of the tips of the other microelectrodes in terms of the axial direction of a bundle of microelectrodes (e.g., FIG. 3(a)). Alternatively, the tips of a plurality of microelectrodes may be disposed at the same position in the axial direction of a bundle of microelectrodes (e.g., FIG. 3(b)). Moreover, each tip may be disposed so that a gap is formed between the side faces of the tips of adjacent microelectrodes (e.g., FIG. 3(a)), or each tip may be disposed so that the side faces of the tips of adjacent microelectrodes are closely attached to each other.

The thickness of a linear core material configuring a microelectrode can be determined according to the disposition of the tips of microelectrodes, which are inserted into a sample when microelectrodes are multi-channeled. For example, when gaps are present among the tips of microelectrodes upon insertion into a sample as described in Example 1, the thickness of a linear core material of a microelectrode preferably ranges from 15 µm to 80 µm. On the other hand, when a plurality of tips of microelectrodes are twisted together or adhere to each other upon insertion into a sample as described in Example 2, for example, the thickness of a linear core material of a microelectrode preferably ranges from 5 µm to 30 µm.

A plurality of multi-channel microelectrodes are provided in an electrically independent manner and thus they can be used to input or output electrical signals independently, as in Examples 1 and 2, for example.

Figure 8:
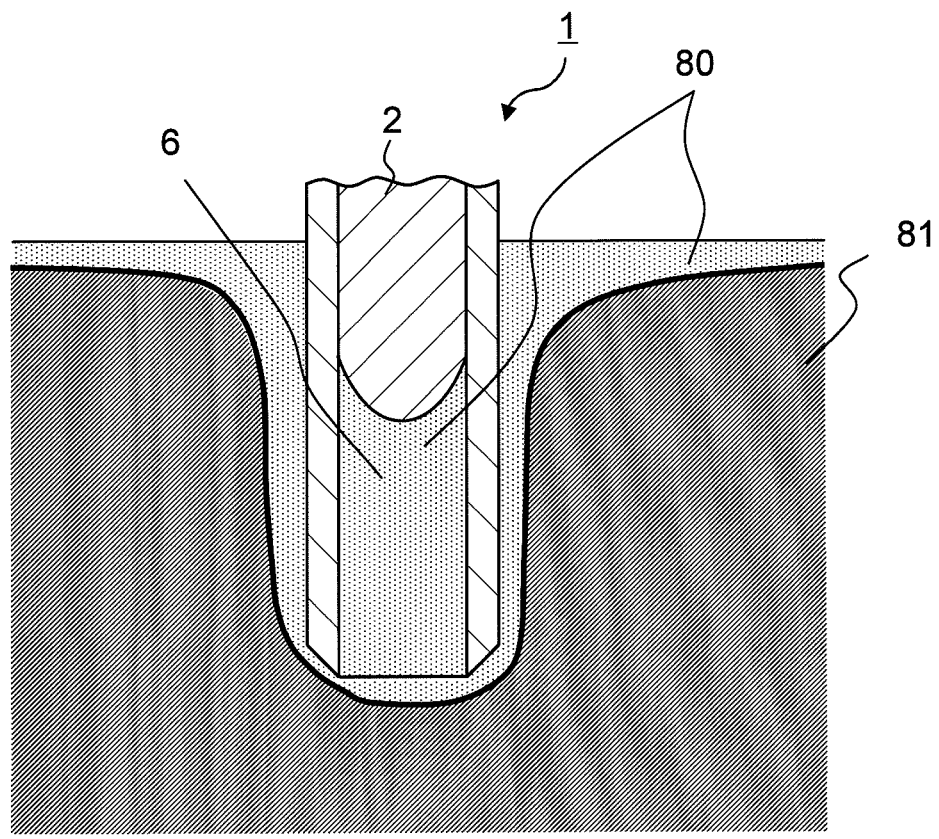
FIG. 8 schematically shows a situation in whichnerve action is measured or nerve cellsneurons are stimulated using the electrodes of the present invention.

Action potentials of nerve cellsneurons can be recorded as large-amplitude waveforms using the microelectrode according to the present invention. It is presumed that this effect is due to the cavity formed in the tip portion of the microelectrode according to the present invention. FIG. 8 schematically shows a situation in which the microelectrode 1 of the present invention is used for measuringnerve action or stimulating nerve cellsneurons. The microelectrode is formed so that nerve tissue 81 containing nerve cellsneurons located outside the cavity 6 and the tip of the linear core material 2 within the cavity 6 communicate with each other via an electrolyte solution 80. The electrolyte solution 80 can be an extracellular fluid within nerve tissue or a prepared artificial cerebrospinal fluid. In a situation in which the microelectrode according to the present invention is used, the electrolyte solution 80 penetrates the cavity 6 from the end part in the extending direction (corresponding to the opening of the cavity 6) of an insulating extending part so that the cavity 6 is filled with the electrolyte solution 80. Also, the electrolyte solution 80 that has penetrated into and filled the cavity 6 comes into contact with electrolyte solution 80 in the periphery of the microelectrode only at the opening of the cavity 6. At this time, a change in ion density, which occurs in the bulk electrolyte solution 80 due tonerve action, causes a change in ion density of the electrolyte solution 80 within the cavity 6 via the end part in the extending direction.

The space within the cavity 6 is isolated from the periphery of the electrode by an insulating coating layer of the outer circumference of the cavity. A change in ion density of the electrolyte solution 80 within the cavity 6 can be detected on the electrode surface unaffectedly from or without affecting the periphery of the electrode.

Furthermore, a plurality of the microelectrodes of the present invention are used in the form of a multi-channel electrode, and the shapes of the tip portions of the microelectrodes are made uniformed, so that electrodes become able to exert performance equivalent to each other and measurement efficiency can be significantly enhanced.

Regarding the structure of a tip part of the microelectrode according to the present invention, structures analogous thereto can be found among conventional electrodes for electrochemical measurement (e.g., see Umeda et. al, Electrochimica Acta, 48 (2003) 1367-1374 FIG. 1). However, such conventional electrode tip parts are used for measurement by filling the cavity of such tip part with a conductive substance such as carbon paste, a catalyst, or the like. Meanwhile, the cavity inside the extending part of the microelectrode according to the present invention is not provided with other elements such as a catalyst or a conductive substance, but rather it functions as a space for containing an electrolyte solution upon use. Various types of measurement using conventional electrodes for electrochemical measurement are intended to capture reactions that take place at the boundary between a filling conductive substance or the like and an electrolyte. Hence, it can be said that the situation of measurement performed using conventional electrodes differs from the same performed using the microelectrode according to the present invention, in terms of technical characteristics. In addition, it is thought that a situation of measurement using such conventional electrodes for electrochemical measurement is analogous to a situation of measurement using a conventionally employed microelectrode having a tip portion with an exposed conductive core material.

The electrode of the present invention can be preferably used as an electrode for measuringnerve action or stimulating nerve cellsneurons. The electrode of the present invention is useful not only as an electrode for measurement of nerve action, but also as an electrode for stimulating nerve cellsneurons.

Figure 9:
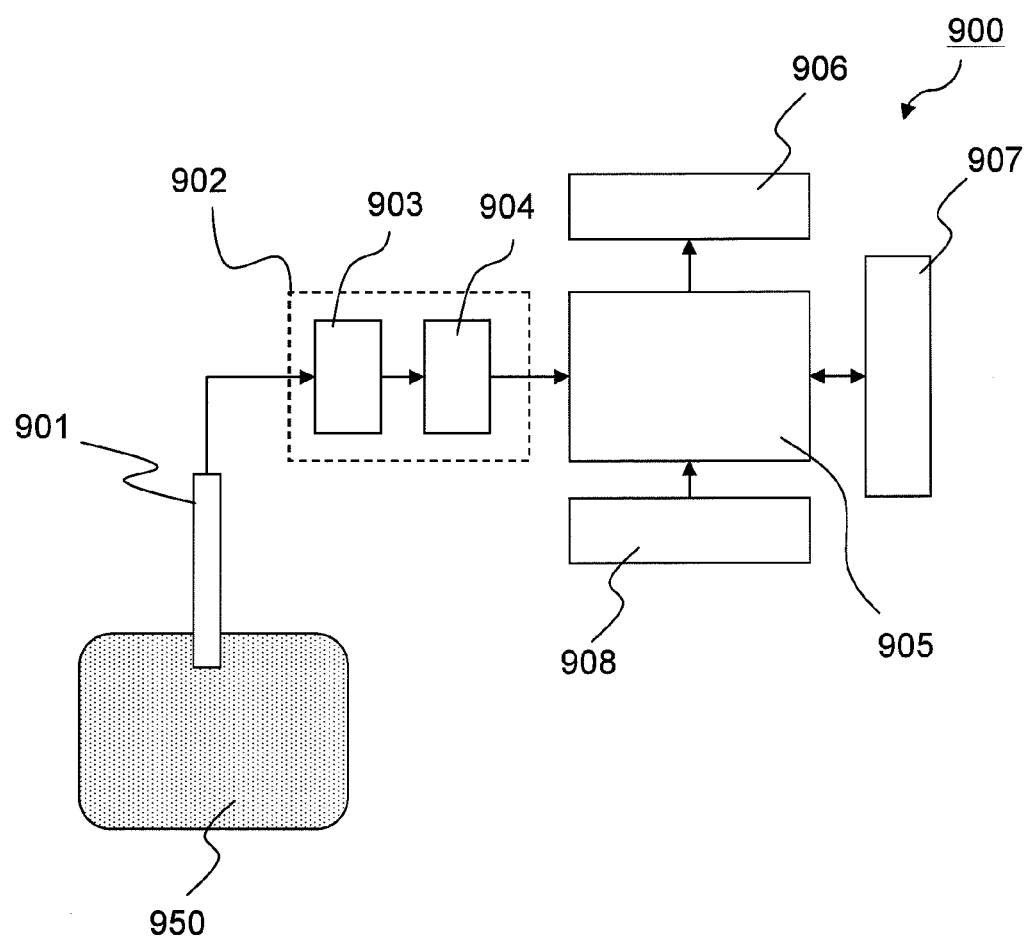
FIG. 9 shows an embodiment of nerve act measuring device comprising the electrodess of the present invention.

FIG. 9 shows the configuration of an embodiment of anerve action measuring device comprising at least one microelectrode of the present invention as an element for measuring nerve action. A nerve action measuring device 900 contains at least one microelectrode 901 of the present invention and an amplifier 902. A microelectrode 901 that is inserted into nerve tissue 950 introduces electric signals (that is, nerve action potentialsaction potentialsneurons) resulting from nerve action to the amplifier 902. The amplifier 902 can be configured from a preamplifier 903 and a main amplifier 904. Output signals from the amplifier 902 are input to an arithmetic processing unit 905. The arithmetic processing unit 905 performs analysis such as waveform analysis based on input signals and then outputs the analytical result to a display device 906. Furthermore, if necessary, the arithmetic processing unit 905 can output analytical results to a memory 907 to store the results. Also, if necessary, the arithmetic processing unit 905 may comprise an input device 908 such as a keyboard. In an embodiment wherein a plurality of microelectrodes 901 are used in combination as a multi-channel electrode, the arithmetic processing unit 905 can independently analyze signals that are introduced from each microelectrode and amplified by an amplifier.

Figure 10:
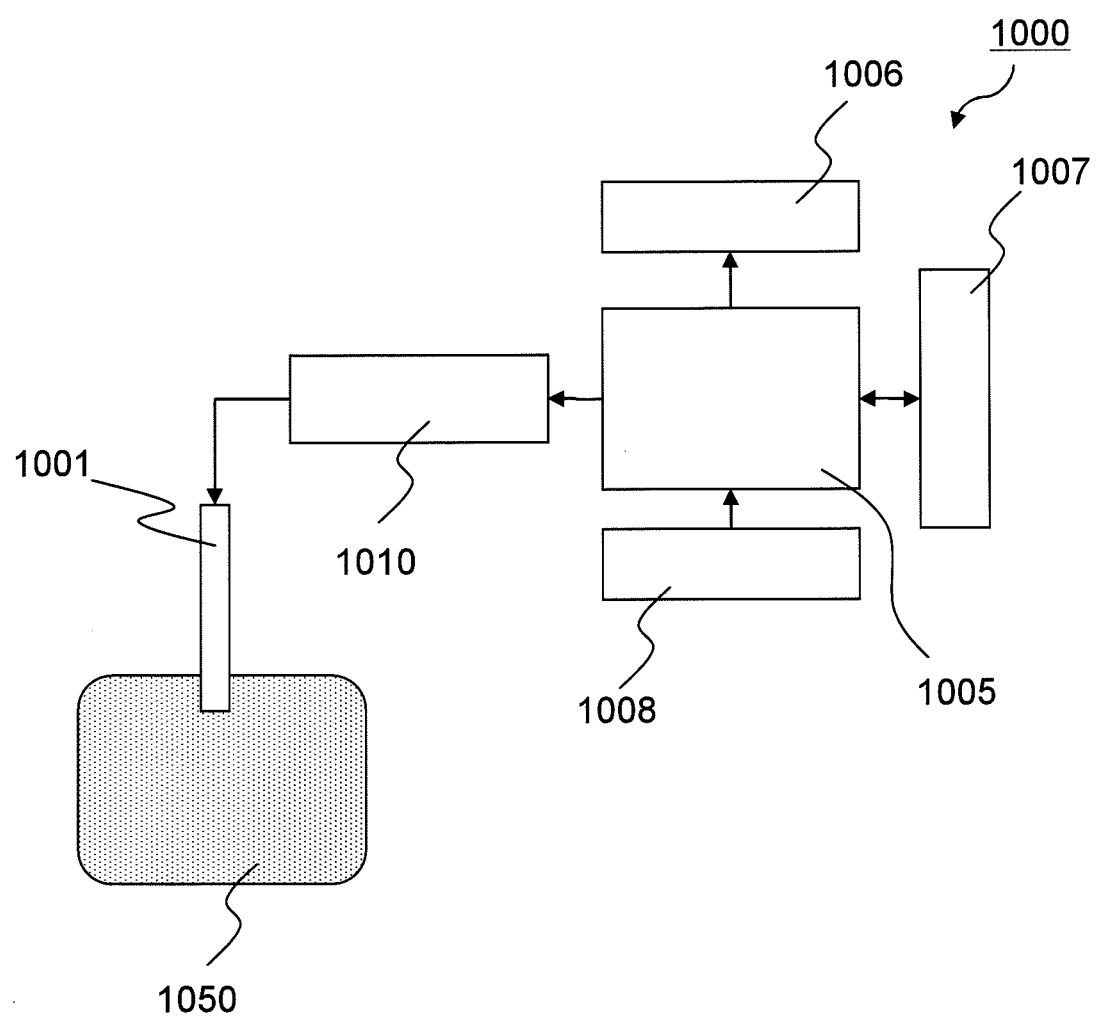
FIG. 10 shows an embodiment of a neuron stimulator comprising the electrodess of the present invention.

FIG. 10 shows the configuration of an embodiment of a neuron stimulator comprising at least one microelectrode of the present invention as an element for stimulating nerve cellsneurons. A neuron stimulator 1000 contains at least one microelectrode 1001 of the present invention and at least an electrical stimulation signal applying device 1010. Electrical stimulation signals applied from the electrical stimulation signal applying device 1010 are transmitted to a nerve tissue 1050 via a microelectrode 1001. The arithmetic processing unit 1005 outputs control signals for controlling the output of electrical stimulation signals to an electrical stimulation signal applying device 1010 based on the information input from the input device 1008. The arithmetic processing unit 1005 can comprise a display device 1006 and a memory 1007, if necessary.

Figure 11:
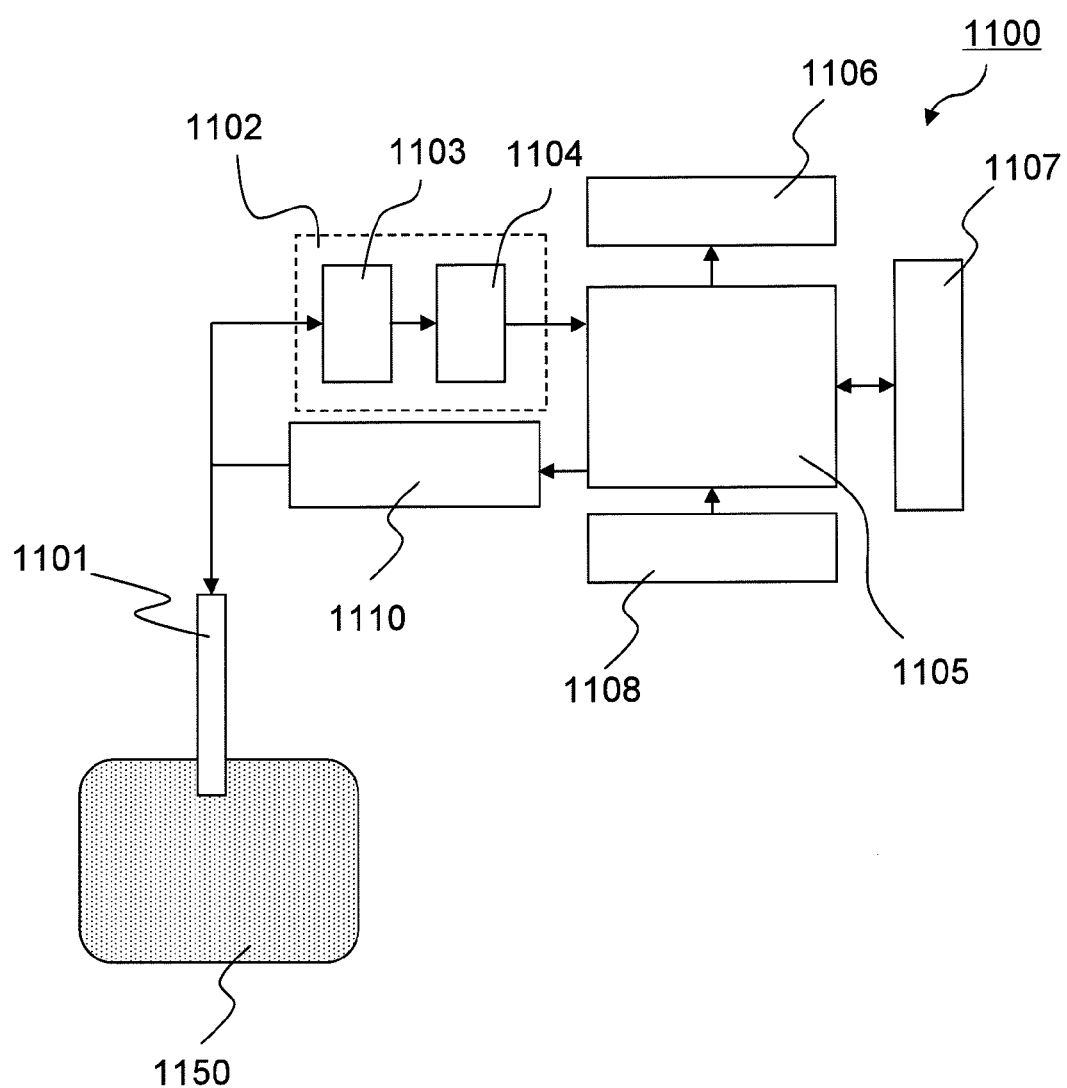
FIG. 11 shows an embodiment of nerve action measuring/neuron stimulating device comprising the electrodess of the present invention.

FIG. 11 shows an embodiment of a nerve action measuring/neuron stimulating device 1100 in which the abovenerve action measuring device and neuron stimulator are integrated. Since constituents in FIG. 11 have the same functions as those of constituents of the same names explained based on FIG. 9 and FIG. 10, explanation of such constituents is omitted.

Figure 2:
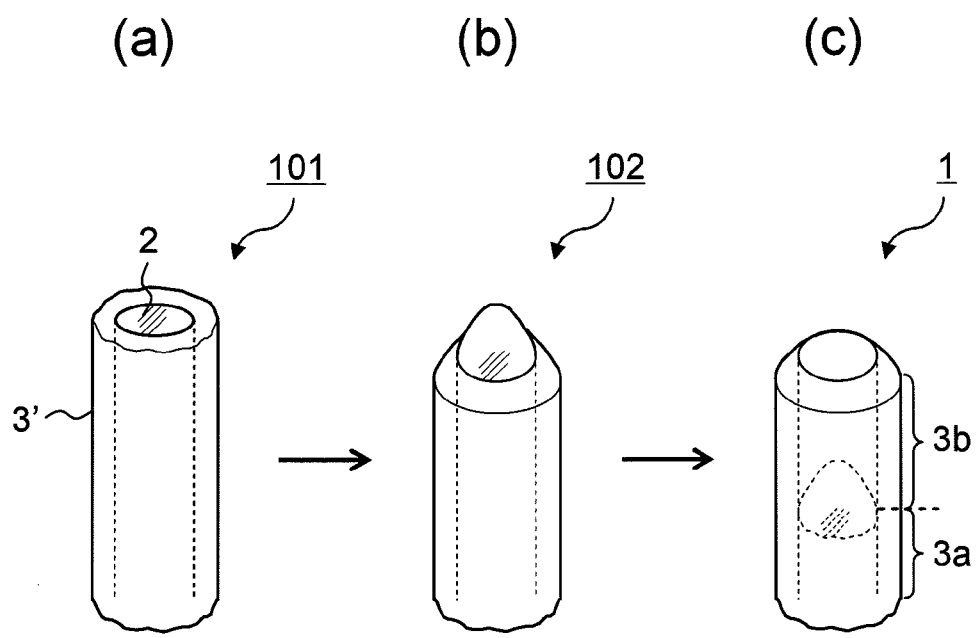
FIG. 2 shows steps for producing an electrode of the present invention.

Next, a method for producing the electrode 1 of the present invention is explained based on FIG. 2.

First, an initial coating layer 3' (finally it comprises a coating layer 3a and an extending part 3b) is formed along the outer circumference of a linear core material 2. For example, the surface of a linear core material 2 such as a nichrome wire is coated with an insulating material such as an epoxy resin, dried at room temperature, and then heated in an oven. This step is repeated according to need, so that the initial coating layer 3' is formed along the outer circumference of the linear core material 2. The linear core material 2 having the initial coating layer 3' is cut using scissors or the like, thereby forming an end part. The thus obtained primary electrode 101 (FIG. 2(*a*)) has been conventionally used as an electrode for the measurement of nerve action. Such end part produced by cutting is not flat or smooth, having a nonuniform structure differing depending on each electrode.

The tip part of the primary electrode 101 is mechanically polished using a electric file or the like, so that a secondary electrode 102 having a tapered structure, in which the outer diameter decreases toward the tip, is obtained (FIG. 2(*b*)).

Subsequently, the linear core material 2 of the secondary electrode 102 is eluted from the tip part by electrolysis, so as to cause the tip to move backward to the inside of the initial coating layer 3'. As a result, a tubular extending part 3b having an inner diameter that is the same as the outer diameter of the linear core material 2 is formed and a cavity 6 is formed therein. In this way, the electrode 1 of the present invention is produced. The electrolysis can be performed by immersing both the tip part of the secondary electrode 102 and a silver wire as a counter electrode in a saline solution or the like, connecting the positive side of a constant current apparatus to the secondary electrode 102 and the negative side thereof to a silver wire, and then turning on electricity. Conditions for turning on electricity can be appropriately determined depending on the thickness of a core material and a constituent material. For example, when a nichrome wire with a diameter of 40 μm is used as a core material, electricity is preferably turned on under conditions of 5 microamperes and 1-60 minutes.

The sharp-pointed electrode 701 of the present invention can also be produced by procedures similar to those in FIG. 2. However, the method employed herein differs from the method shown in FIG. 2 in that polishing is performed to form a single plane inclined toward the shaft center of the linear core material at the tip part during the step of mechanical polishing using an electric file or the like.

EXAMPLE 1

The electrode 1 of the present invention was actually produced and compared with a conventional electrode (primary electrode 101) as per the following Example.

1. Production of Electrode 1.1. Production of Epoxy Coating Film

A nichrome wire with a diameter of 40 μm was cut to have a length of 15 cm, a weight was applied at the lowermost part, and then the wire was hanged vertically. A brush containing epoxy was applied to the nichrome wire, the nichrome wire was moved downward by a necessary length, and then the brush was moved away from the wire. A similar procedure was performed again, with the direction varied by 180°. The nichrome wire was dried at room temperature for about 5 minutes, placed in an oven, heated at 100° C. for 20 minutes, and then further heated at 180° C. for 30 minutes. This procedure (coating to heating) was repeated 10 times. The thickness of the thus obtained epoxy coating film was 12 μm. One end of the film was cut using scissors, so that a primary electrode was produced. In addition, the cross-section of a nichrome wire used in this Example was almost a true circle.

1.2. Mechanical Polishing

Diamond powder fixed to the tip of a small motor shaft was brought into contact with the tip of the primary electrode obtained in 1.1 above via high-speed rotation. The stereoscopic positional relationship between the small motor and the electrode was gradually shifted, so that a secondary electrode with a tapered tip was obtained.

1.3. Electrolyte

The tip part of the secondary electrode obtained in 1.2 and a silver wire as a counter electrode were immersed together in a saline solution or the like. The positive side and the negative side of the constant current apparatus were connected to the secondary electrode and the silver wire, respectively, and then electricity was turned on. Electricity was turned on at 5 microamperes for 12 minutes. Thus, a cavity having a depth of 110 micrometers was formed at the tip of the thus obtained electrode of the present invention.

2. Measurement of Action Potentialss of Nerve Cellss

Action potentialss of nerve cellss were measured using the electrode of the present invention obtained in 1 above and the primary electrode prepared at the end of 1.1 above. Hereafter, the electrode of the present invention and the primary electrode may be collectively referred to as a "microelectrodes."

Figure 3:
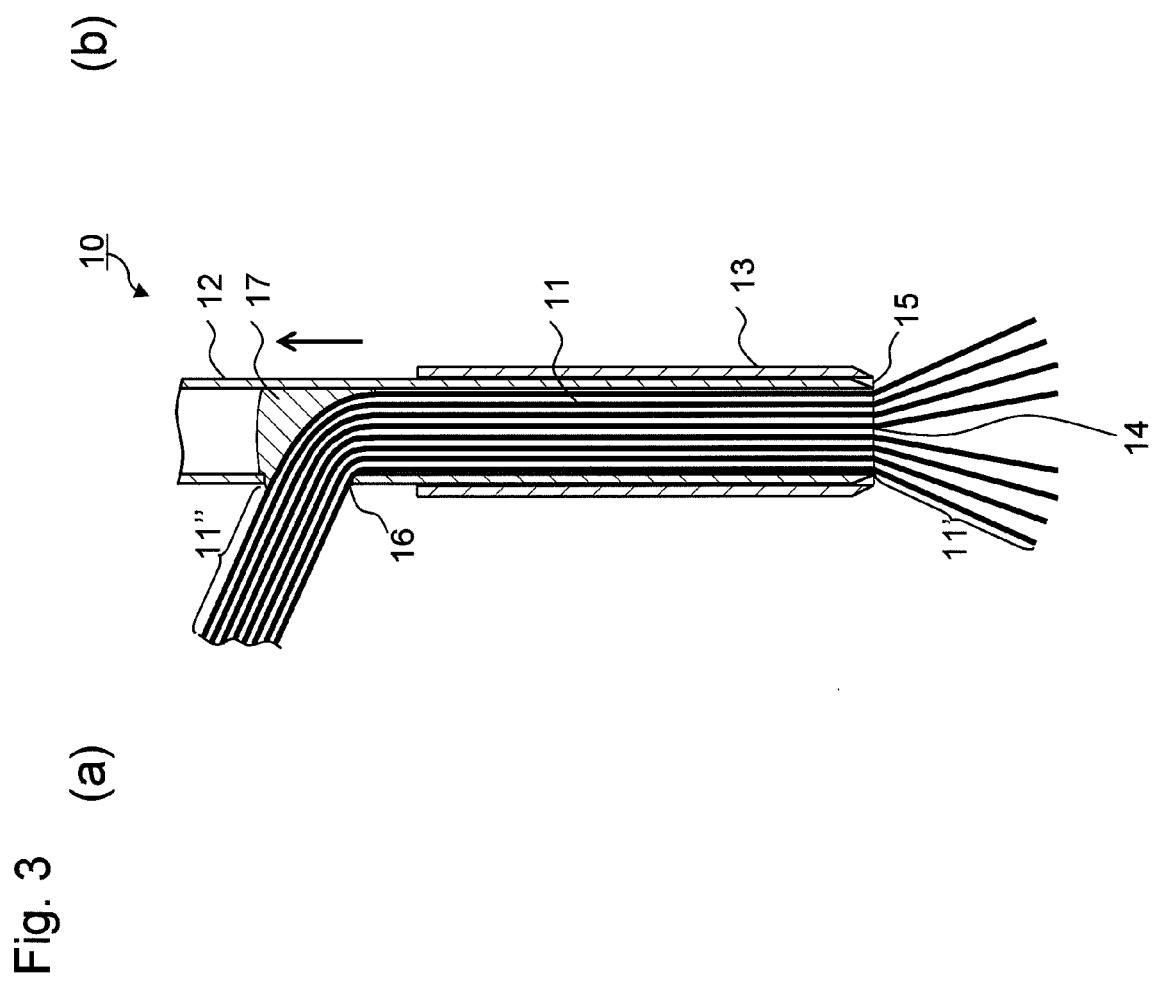
FIG. 3 shows schematic cross-sectional views of the tip portion of a device for fine-adjusting multi-channel electrodes comprising a plurality of microelectrodes (8 microelectrodes), which was produced and used in Examples.

The structure and functions of a multi-channel electrode fine-adjusting device 10 containing eight microelectrodes 11, which was used in this experiment, are explained based on FIGS. 3 and 4.

The multi-channel electrodefine-adjusting device 10 comprises at least a plurality of (eight microelectrodes in this example) microelectrodes 11, an internal sheath tube 12, and an external sheath tube 13. The internal sheath tube 12 is a hollow tubular member having a tip opening 14 on one end. The external sheath tube 13 is a hollow tubular member having a tip opening 15 on one end. The inner diameter of the external sheath tube 13 is the same as or slightly larger than the outer diameter of the internal sheath tube 12. The length of the external sheath tube 13 is shorter than that of the internal sheath tube 12. A portion on the tip opening 14 side of the internal sheath tube 12 (hereinafter, simply referred to as the "tip portion of an internal sheath tube") was inserted into the external sheath tube 13, so that the tip opening 14 and the tip opening 15 were oriented in the same direction and they can reciprocate along the longitudinal direction. A sidewall opening 16 for communication of the internal space of the internal sheath tube 12 with the outside is made through a side wall of a portion (hereinafter, simply referred to as the "rear end portion of an internal sheath tube") of the internal sheath tube 12 on the side of the opposite end from the tip opening 14 of the internal sheath tube 12. A plurality of microelectrodes 11 are disposed by fixing the microelectrodes 11 within the internal space of the internal sheath tube 12, so that the tip treated in 1 above protrudes from the tip opening 14 (hereinafter, protruding portions are referred to as "protruding portions 11'") and the other end (hereinafter, referred to as "rear end portion 11" of microelectrode") appears outside from the side wall opening 16. At this time, the protruding portions 11' of a plurality of microelectrodes 11 are each bent near the tip opening 14 of the internal sheath tube 12, so that protruding portions 11' are oriented to directions at an angle within the range of less than 90°, differing from the opening direction of the tip opening 14. The microelectrodes 11 are fixed within the internal sheath tube 12 by injecting an adhesive 17 from the side wall opening 16. Furthermore, an adhesive is also injected from the tip opening 14 into the internal sheath tube 12 in which microelectrodes 11 have been inserted, so that microelectrodes 11 are fixed in the internal sheath tube 12 also near the tip opening 14 (not shown because of overlapping with microelectrodes 11). When the opening 15 side end (external sheath tube tip) of the external sheath tube 13 is located more closely to the tip side compared with the opening 14 side end (internal sheath tube tip) of the internal sheath tube 12 along the longitudinal direction of the internal sheath tube, and when the distance L between the internal sheath tube tip and the external sheath tube tip is smaller than the length of the wire-shaped electrode protruding portions 11', the tips of the electrode protruding portions 11' are partially exposed outside. When the external sheath tube tip and the internal sheath tube tip are located at the same position along the longitudinal direction of the internal sheath tube, or, when the external sheath tube tip is located more closely to the rear end side compared with the internal sheath tube tip along the longitudinal direction of the internal sheath tube, all electrode protruding portions 11' are externally exposed. FIG. 3(*a*) shows such a situation in which the external sheath tube tip and the internal sheath tube tip are located at the same position along the longitudinal direction of the internal sheath tube. FIG. 3(*b*) shows such a situation in which the external sheath tube tip is located more closely to the tip side compared with the internal sheath tube tip along the longitudinal direction of the internal sheath tube and the length L (distance) is the same as the length of the protruding portions 11'. At this time, the wire-shaped electrode protruding portions 11' are contained within the external sheath tube 13 and are not exposed outside.

The entire structure of a multi-channel electrode fine-adjusting device 10 is explained based on FIG. 4, which comprises a positioning means for freely adjusting the protruding length of the microelectrodes 11 by freely adjusting the position of the internal sheath tube 12 relative to the external sheath tube 13. A first support plate 21 and a second support plate 22 are vertically fixed and mounted on the rear end portion of the internal sheath tube 12 and the external sheath tube 13, respectively. Two bolt shaft insertion holes are made in the first support plate 21 and the second support plate 22 and specifically made at positions that face each other when the first support plate 21 and the second support plate 22 are caused to face each other. Two bolts 23 and 23 are disposed in parallel through the above bolt shaft insertion holes, so that each head part is positioned on the side of the second support plate 22 and each shaft part is located on the side of the first support plate 21. The head parts of bolts 23 and 23 are fixed on the second support plate 22 by tightening the nuts 24 and 24 for fixation of bolt head parts on the side of the second support plate 22. Nuts 25 and 25 for supporting springs, which support the ends of springs 26 and 26 (described later), are further threadably mounted more closely to the shaft end side compared with the nuts 24 for fixation of bolt head parts of the bolts 23 and 23. The urging springs 26 and 26 are disposed between the surface of the bolt shaft end side of the nuts 25 and 25 for supporting springs and the surface on the bolt head part of the first support plate 21. The urging springs 26 and 26 separately press the first support plate 21 toward the bolt shaft end direction. Position-determining nuts 27 and 27 are threadably mounted more closely to the shaft end side compared with the first support plate 21 of the bolts 23 and 23. The position-determining nuts 27 and 27 are turned in the tightening direction, so that the internal sheath tube 12 fixed to the first support plate 21 can be sent out to the tip direction of the external sheath tube 13. Meanwhile, the position-determining nuts 27 and 27 are turned in the loosening direction, so that the internal sheath tube 12 can be moved backward in the opposite direction. FIG. 4(*a*) shows a situation in which the position-determining nuts 27 and 27 are loosened. At this time, the protruding portion 11' of the microelectrodes is entirely contained in the external sheath tube 13. The internal structure of the tip in FIG. 4(*a*) corresponds to that in FIG. 3(*b*). FIG. 4(*b*) shows a situation in which the position-determining nuts 27 and 27 are tightened. At this time, the protruding portions 11' of the microelectrodes are exposed to the outside via the tip opening 15 of the external sheath tube 13. The internal structure of the tip in FIG. 4(*b*) corresponds to that in FIG. 3(*a*). Through appropriate adjustment of the tightening positions for the position-determining nuts 27 and 27 in this manner, the protruding amount of the protruding portions 11' (of the microelectrodes) from the external sheath tube 13 can be freely adjusted. In addition, although not shown in FIGS. 3 and 4 for abbreviation, the electrode rear end portion 11" is electrically connected to an apparatus for measuring changes in potentials.

In this Example, a stainless steel tube having an inner diameter of 0.6 mm and an outer diameter of 0.3 mm was used as an internal sheath tube 12, and a stainless steel tube having an inner diameter of 0.9 mm and an outer diameter of 0.6 mm was used as an external sheath tube 13. As microelectrodes 11, eight electrodes of the present invention obtained in 1 above or eight primary electrodes were used. The length of the protruding portions 11' of microelectrodes was 7 mm. In the case of the apparatus used in this Example, the bundle of the protruding portions 11' of microelectrodes does not radiate if the length (movement distance) of the protruding portions 11' exposed outwardly from the tip opening 15 of the external sheath tube 13 is about a maximum of 3 mm. If the protruding portions 11' are moved by more than such distance, the bundle gradually radiates.

First, the tip of the external sheath tube 13 was inserted into the brain of a rat while the external sheath tube 13 completely contained microelectrodes 11 (specifically, the situation shown in FIG. 4(*a*)). Specifically, the rat was anesthetized with pentobarbital (50 mg/kg) and then fixed to a brain stereotaxic apparatus. A roughly 2-mm hole was bored through the skull at a point 2 mm behind the bregma and 0.5 mm to the right of the midline. The tip of the external sheath tube 13 was inserted to a depth of 5.5 mm from the brain surface. The tip was fixed with an acrylic resin while being inserted therein. The tip of the external sheath tube 13 was located at a position 2 mm above the hypothalamic paraventricular nucleus. Before recovery from anesthesia, a preamplifier for recording was connected to the rear end portion 11" of microelectrodes via a connector.

At about 3 days after sufficient recovery of the rat, the microelectrode tips were projected outward by turning alternately the two position-determining nuts 27 and 27 in the tightening direction. Recording was performed while moving the microelectrode tips closer to a target site. The point to which the microelectrode tips were moved by 3 mm was designated as the end point.

Figure 5:
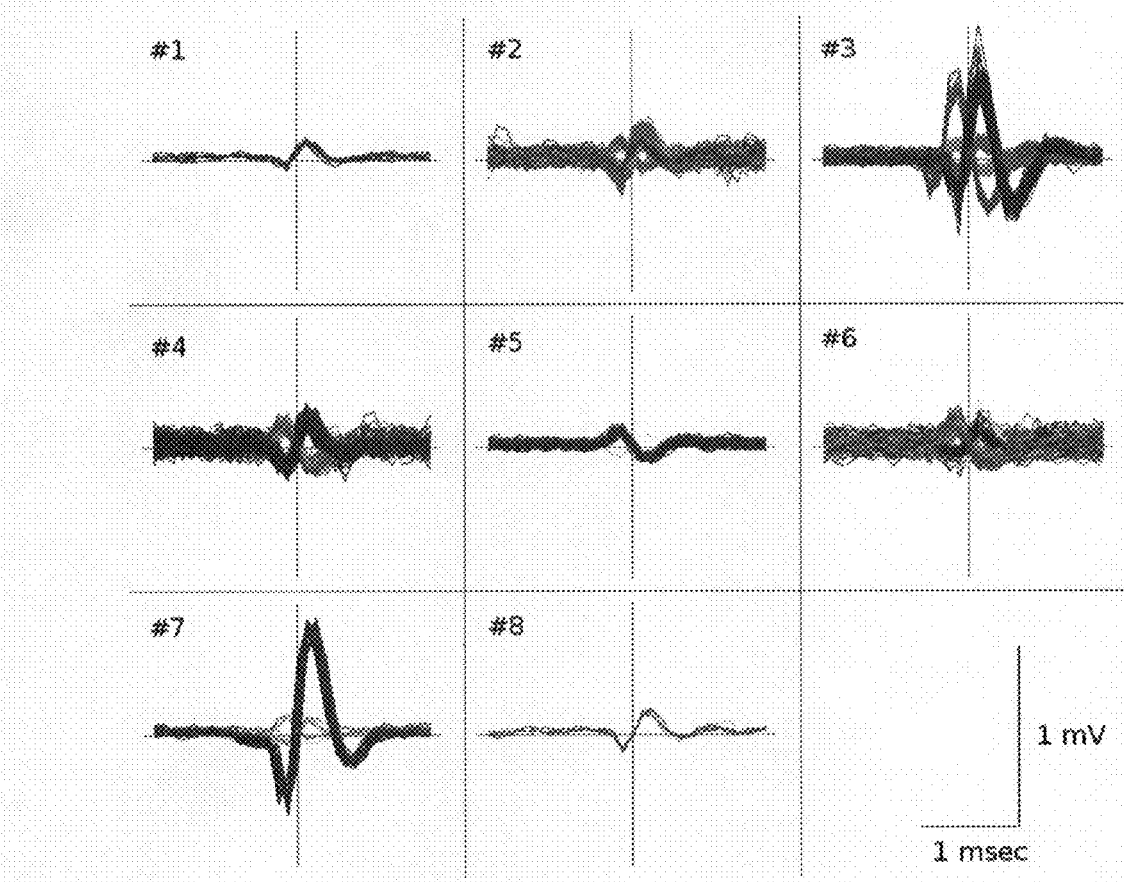
FIG. 5 shows the results for each electrode when nerve action potentialsaction potentialsneurons were measured with a combination of the 8 electrodes of the present invention.
Figure 6:
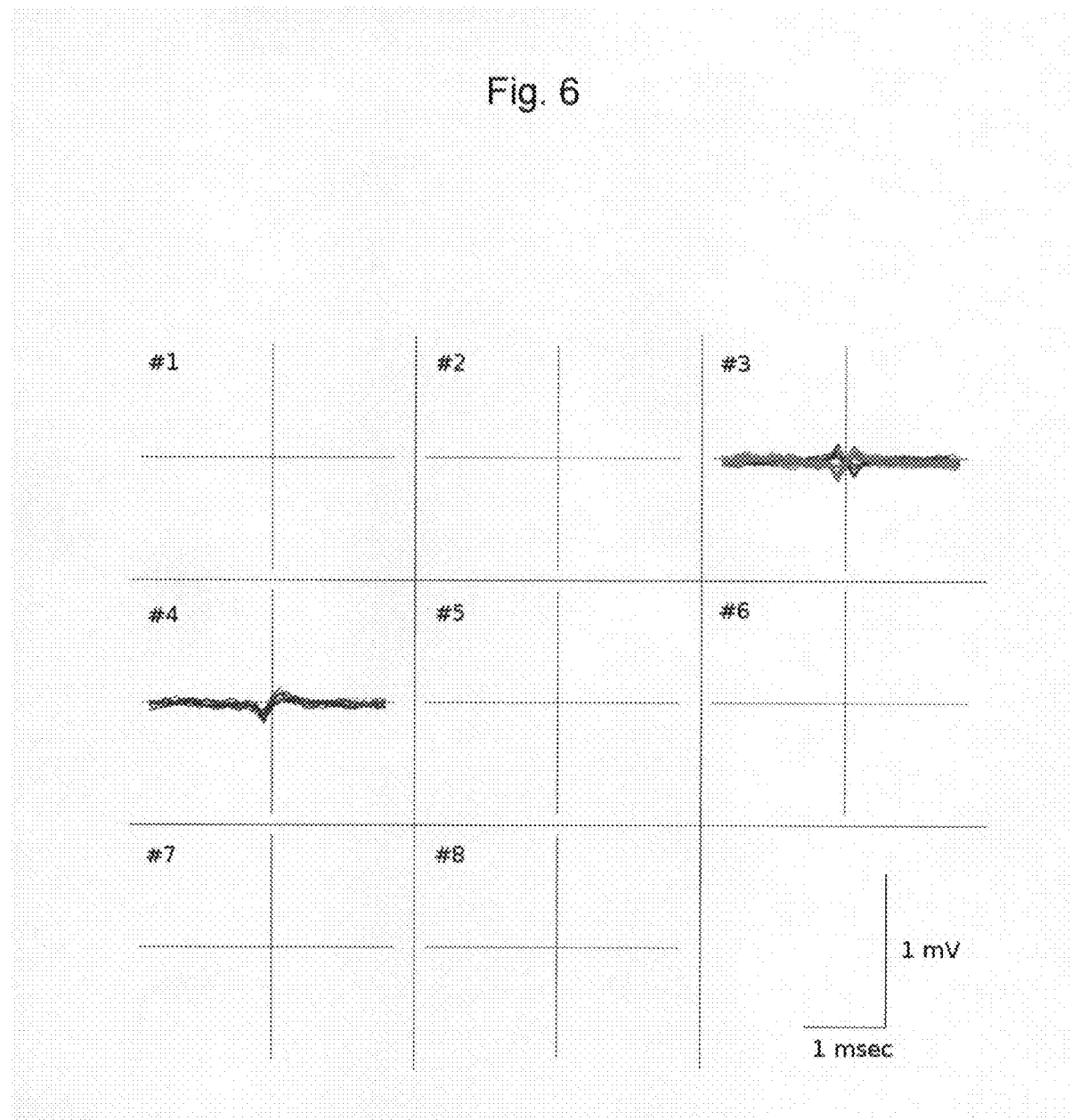
FIG. 6 shows the results for each electrode when nerve action potentialsaction potentialsneurons were measured with a combination of 8 conventional electrodes for measurement of nerve actio.

FIG. 5 shows an example of the measurement results obtained using the electrode of the present invention, and FIG. 6 shows an example of the measurement results obtained using the primary electrode (conventional electrode). In both FIGS. 5 and 6, action potentials having amplitudes of a certain level or higher were cut and then superimposed for each electrode (#1-#8).

Activity of a maximum amplitude of 1.5-mV could be recorded by 6 to 7 out of 8 electrodes of the present invention. As shown in examples in FIG. 5, activity of about 1 mV could be recorded simultaneously by #3 and #7. In the case of 6 electrodes other than #3 and #7, activity of 100-200 microvolts could be recorded more than once. Also, during simultaneous movement of 8 electrodes by 3 mm within the brain, activity equivalent to 1 mV was recorded by the electrodes other than #3 and #7. Nerve action was seamlessly recorded by each electrode during movement, although the amplitude fluctuated.

A waveform with an amplitude ranging from about 100 to 200 microvolts was recorded only by 1 to 3 (#3 and #4 in FIG. 6) out of 8 conventional primary electrodes. Also, when 8 electrodes were simultaneously moved by 3 mm using the electrode fine-adjusting device, nerve action was recorded only several times by specific electrodes (#3 and #4 in FIG. 6) alone.

EXAMPLE 2

Hereafter, an Example is described wherein a sharp-pointed microelectrode 701 was produced using a 6.5-μm tungsten wire and then extracellular action potentials were recorded from brain slice samples.

In this Example, samples to be measured were prepared by slicing the brain removed immediately after anaesthesia of an animal to result in slices each having a thickness of 400 μm using a dedicated slicer. The samplesa was eachsubjected to recording by lightlypressing each electrode to the surface of each slice sample while performing perfusion using artificial cerebrospinal fluid and confirming nerve cells An epoxy resin coating film was formed on the outer circumference of a 6.5-μm tungsten wire by a method similar to the method described in 1.1 in Example 1. The thickness of the thus obtained epoxy coating film was 3 μm. In addition, the cross-section of the tungsten wire used in this Example was almost a true circle. Three or seven tungsten wires were bundled together and then the central part of the resultant bundle was tied with a thin thread. To unify them, a brush impregnated with epoxy was applied again for coating, gaps in the bundle were filled in, and then the bundle was cured by heating at 100° C. for 30 minutes and at 180° C. for 30 minutes. At this time, the procedure was carefully performed, so as not to allow epoxy to reach the portion to be used as an electrode tip (or so as not to unnecessarily thicken the portion to be used as an electrode tip).

After curing, the end part of electrodes was inclined toward a grindstone so that it came into contact with the grindstone. A single oblique end surface slanted relative to the wire shaft center was formed on the end part and then the end part was processed to have a sharpened tip part. The inclination angle was determined to be 30°, which was the same as the angle at which electrodes were applied to each brain slice sample.

After completion of mechanical polishing, electricity was turned on at a current of 1 μA for 5 minutes, so that electrolytic polishing was performed. Thus, an electrode comprising a bundle of several sharply pointed microelectrodes 701 was obtained as shown in FIG. 7.

The thus obtained sharply pointed microelectrodes forming a bundle were mounted on a 3-dimensional manipulator and then lightly applied (pressed) to the surface of a brain slice sample. Thus, it was confirmed that extracellular action potentials could be recorded.

EXAMPLE 3

Confirmation of Electrode Characteristics

The electrode characteristics of the electrode 1 of the present invention obtained by a procedure similar to that of the method of 1 above in Example 1 were confirmed by impedance measurement. However, instead of turning on electricity for 12 minutes at 5 microamperes as in 1.3 above, electricity was turned on in this experiment at 5 microamperes for 3 minutes, 15 minutes, 20 minutes, 30 minutes, or 50 minutes. Impedance measurement was performed by immersing the electrode of the present invention in physiological saline while varying the frequency from 10 Hz to 100 kHz using sine wave signals at a constant voltage of 10 mV (Hioki, LCR meter 3522-50). For comparison, a primary electrode at the completion of 1.1 above and a secondary electrode at the completion of 1.2 above were used.

Figure 12:
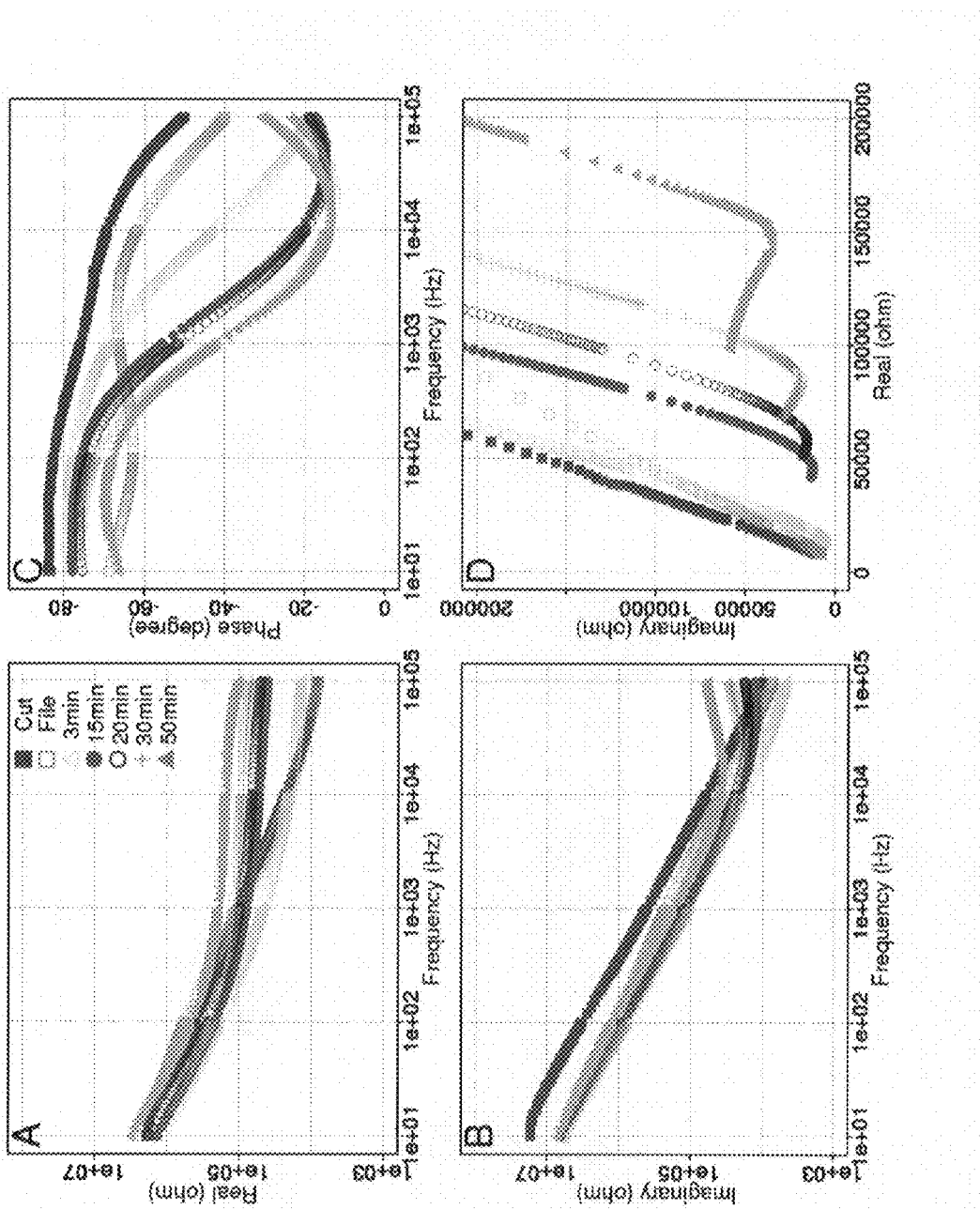
FIG. 12 shows the results of measuring the characteristics of the electrodes of the present invention by impedance measurement.

Since the duration of each action potential was around 1 msec, impedances at a frequency of 1 kHz were compared, as shown in Table 1. Also, FIG. 12 shows measurement results.

It was confirmed in the case of the electrode of the present invention that the impedance significantly decreased compared with the case of the primary electrode. It was also confirmed based on a measurement example shown in FIG. 12D that electrode characteristics can be varied based on the electrolysis time (3, 15, 20, 30, or 50 minutes). Here, in view of generation of a cavity by the electrolysis of 1.3 above, a relationship between the cavity and electrode characteristics is strongly suggested based on such measurement results.

TABLE 1

| | Impedance measured at 1 kHz/ohm | Ratio of minimum length in the extending direction to linear core material diameter |
|---|---|---|
| Primary electrode (comparison) | $4.23 \times 10^5$ | |
| Secondary electrode (comparison) | $2.43 \times 10^5$ | |
| Electrode of the present invention (electrolysis time: 3 minutes) | $1.23 \times 10^5$ | About 0.7 times |
| Electrode of the present invention (electrolysis time: 15 minutes) | $1.43 \times 10^5$ | About 2.7 times |
| Electrode of the present invention (electrolysis time: 20 minutes) | $1.64 \times 10^5$ | About 3.4 times |
| Electrode of the present invention (electrolysis time: 30 minutes) | $1.59 \times 10^5$ | About 5.5 times |
| Electrode of the present invention (electrolysis time: 50 minutes) | $2.59 \times 10^5$ | About 8.5 times |

All publications, patents, and patent applications cited herein are incorporated herein by reference in their entirety.

The invention claimed is:
1. An electrode, comprising:
a conductive linear core material;
an insulating coating layer with which the outer circumference of the linear core material is coated; and
an extending part formed by extending the end part of the insulating coating layer on one tip side of the linear core material beyond the tip in the longitudinal direction of the linear core material, and a cavity opening in the extending direction is formed within the extending part, wherein the outer diameter of the tip part of the linear core material decreases toward the tip direction within the cavity opening.

2. The electrode according to claim 1, which is used for measuring neural activity or stimulating neurons.

3. The electrode according to claim 1, wherein an end in the extending direction of the extended part is located on a single plane vertical to the shaft center of the linear core material and is formed so that the outer diameter of the end part in the extending direction of the extended part decreases along the extending direction.

4. The electrode according to claim 1, wherein the end part in the extending direction of the extended part is sharply pointed.

5. The electrode according to claim 1, wherein the minimum length of the inner surface of the extended part along the extending direction is 0.1 to 10 times the thickness of the linear core material.

6. The electrode according to claim 1, wherein the thickness of the linear core material ranges from 5 μm to 80 μm.

7. The electrode according to claim 2, wherein neurons located outside the cavity opening and the tip of the linear core material within the cavity opening are caused to communicate with each other via an electrolyte solution when the electrode is used for measuring neural activity or stimulating neurons.

8. A multi-channel electrode, comprising a combination of a plurality of the electrodes according to claim 1.

9. A neural activity measuring device, comprising at least one electrode according to claim 1 as an element for measuring neural activity.

10. A neuron stimulator, comprising at least one electrode according to claim 1 as an element for stimulating neurons.

* * * * *